United States Patent [19]

Kanner et al.

[11] Patent Number: 5,572,997
[45] Date of Patent: Nov. 12, 1996

[54] COAGULATION TIMER

[75] Inventors: Rowland W. Kanner, Guntersville; Fred E. Williams, Jr., Arab, both of Ala.

[73] Assignee: Ryder International Corporation, Arab, Ala.

[21] Appl. No.: 259,517

[22] Filed: Jun. 14, 1994

[51] Int. Cl.$^6$ .................................................. A61B 5/00
[52] U.S. Cl. .............................. 128/637; 604/1; 128/755; 128/DIG. 22
[58] Field of Search ..................... 422/58, 61; 604/1–3; 128/637, 755, DIG. 22

[56] References Cited

U.S. PATENT DOCUMENTS

| | | | |
|---|---|---|---|
| 3,724,463 | 4/1973 | Vail | 604/1 |
| 3,818,911 | 6/1974 | Fournier | 604/1 |
| 5,358,480 | 10/1994 | Melcher et al. | 604/1 |

FOREIGN PATENT DOCUMENTS

| | | | |
|---|---|---|---|
| 8910156 | 11/1989 | WIPO | 604/3 |

*Primary Examiner*—Angela D. Sykes
*Assistant Examiner*—Robert L. Nasses, Jr.
*Attorney, Agent, or Firm*—Trexler, Bushnell, Giangiorgi & Blackstone, Ltd.

[57] ABSTRACT

A coagulation timer device is used to monitor the bleeding time of a patient to determine the amount of time required to achieve clotting. The coagulation timer device includes a carrier member, a linearly oriented absorbing medium which is affixed to the carrier member and a bag member which overlays the carrier member and the medium. The medium, such as filter paper or the like, is used to blot blood from an incision which has been formed through the skin. The medium is affixed to the carrier member and includes a plurality of segments each of which are defined by a scalloped edge portion which extends beyond the edges of the carrier member. The segments are used one at a time at predetermined intervals to blot the blood by touching the scalloped edge to the blood. Indicia is provided on the carrier member to let a medical person or technician know where the medium should be touched to the blood at each predetermined interval and provides a quick reference guide to let the technician know the amount of time that it has taken for the blood to clot. The bag member is affixed to the carrier member and is retractable to uncover the medium, while being replaceable to cover the medium.

11 Claims, 3 Drawing Sheets

COAGULATION TIMER

BACKGROUND OF THE INVENTION

This invention is generally directed to a coagulation timer device for monitoring the bleeding time of a patient by administering an incision through the skin and then blotting the blood at predetermined intervals to determine the amount to time necessary for the patient to achieve clotting. More particularly, this invention is directed to a coagulation timer device which minimizes the risk of contact of the patient's blood by a medical technician or person who is monitoring the clotting time.

Before a patient undergoes surgery, a surgeon needs to know the amount of time that is needed for the patient's blood to clot so as to minimize possible problems which could occur during and after surgery. Coagulation timers are commonly used to measure the clotting time of a patient.

One example of a known prior art coagulation timer is a disc-shaped piece of blotter paper. To measure the clotting time, a controlled or predetermined incision is made on the inside of the forearm of a patient, approximately five centimeters below the antecubital crease. Devices for making such a controlled incision are known in the art, two examples of which can be found is U.S. Pat. Nos. 4,078,552 and 4,735,203. A timer is started to measure the amount of time for clotting. At prescribed intervals the medical technician touches the disc-shaped piece of paper to the blood which results from the incision and wicks the blood. The disc is rotated and the technician, after a predetermined amount of time, touches an unadulterated portion of the disc to the blood and wicks the blood. The disc is again rotated and the procedure is repeated until the blood no longer stains the blotter paper. After the bleeding has stopped, the timer is shut off. The bleeding time is the amount from when the timer was started to when it was shut off.

One problem with this type of coagulation timer is that the technician who administers the test risks contact with the patient's blood since the blood is left exposed during the test. Another known prior art coagulation timer has the disc housed within a bag. The bag is torn open to expose a portion of the disc. After each time the blood is wicked, the stained portion of the disc is rotated by the technician into the bag.

While this second type of coagulation timer reduces somewhat the risk of contact with the patient's blood, a possibility still exists that the technician may come into contact with the blood. More specifically, when the disc is grasped to be rotated, the technician could inadvertently grasp a stained portion of the disc. Also, the stained portion can come into contact with the edge of the bag when the disc is rotated and some blood may smear onto the bag thereby exposing the medical technician to possible contact. Furthermore, the disc is sometimes difficult to rotate into the bag and since a disc shape is used, blotter paper is wasted. Also, proper use of this second type timer arrangement requires that care be taken in opening the bag properly. If the bag is destroyed during opening, it is not available to provide a shield or protection for the technician.

The present invention is intended to minimize a medical person's or technician's risk of contact with a patient's blood when the clotting time is measured as well as to present several other improvements over prior art coagulation timers.

OBJECTS AND SUMMARY OF THE INVENTION

A general object of the present invention is to provide a coagulation timer device which is used to monitor the bleeding time of a patient by administering an incision through the skin and then blotting the blood at predetermined intervals with the coagulation timer device to determine the amount of time necessary to achieve clotting.

An object of the present invention is to provide a coagulation timer device which includes a linearly oriented absorbing medium.

Another object of the present invention is to provide a coagulation timer device which minimizes the risk of contact of the patient's blood by a medical person who is monitoring the clotting time.

Briefly, and in accordance with the foregoing, the present invention discloses a coagulation timer device which is used to monitor the bleeding time of a patient to determine the amount of time required to achieve clotting. The coagulation timer device includes a carrier member, a linearly oriented absorbing medium which is affixed to the carrier member and a bag member which overlays the carrier member and the medium. The carrier member includes a handle and a linear portion extending therefrom. The medium, such as filter paper or the like, is used to wick blood from an incision which has been formed through the skin. The medium is affixed to the linear portion and includes a plurality of segments each of which are defined by a scalloped edge portion which extends beyond the edges of the linear portion. The segments are used one at a time at predetermined intervals to blot the blood by touching the scalloped edge to the blood. Indicia is provided on the linear portion of the carrier member to let a technician know where the medium should be touched to the blood during the measurement of the patient's clotting time and provides a quick reference guide to let the technician know the amount of time that it has taken for the blood to clot. The bag member is affixed to the handle and is retractable around the handle to uncover the medium, while being replaceable to cover the medium, intermediate each instance of wicking of the blood.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE PREFERRED EMBODIMENT

Figure 1:
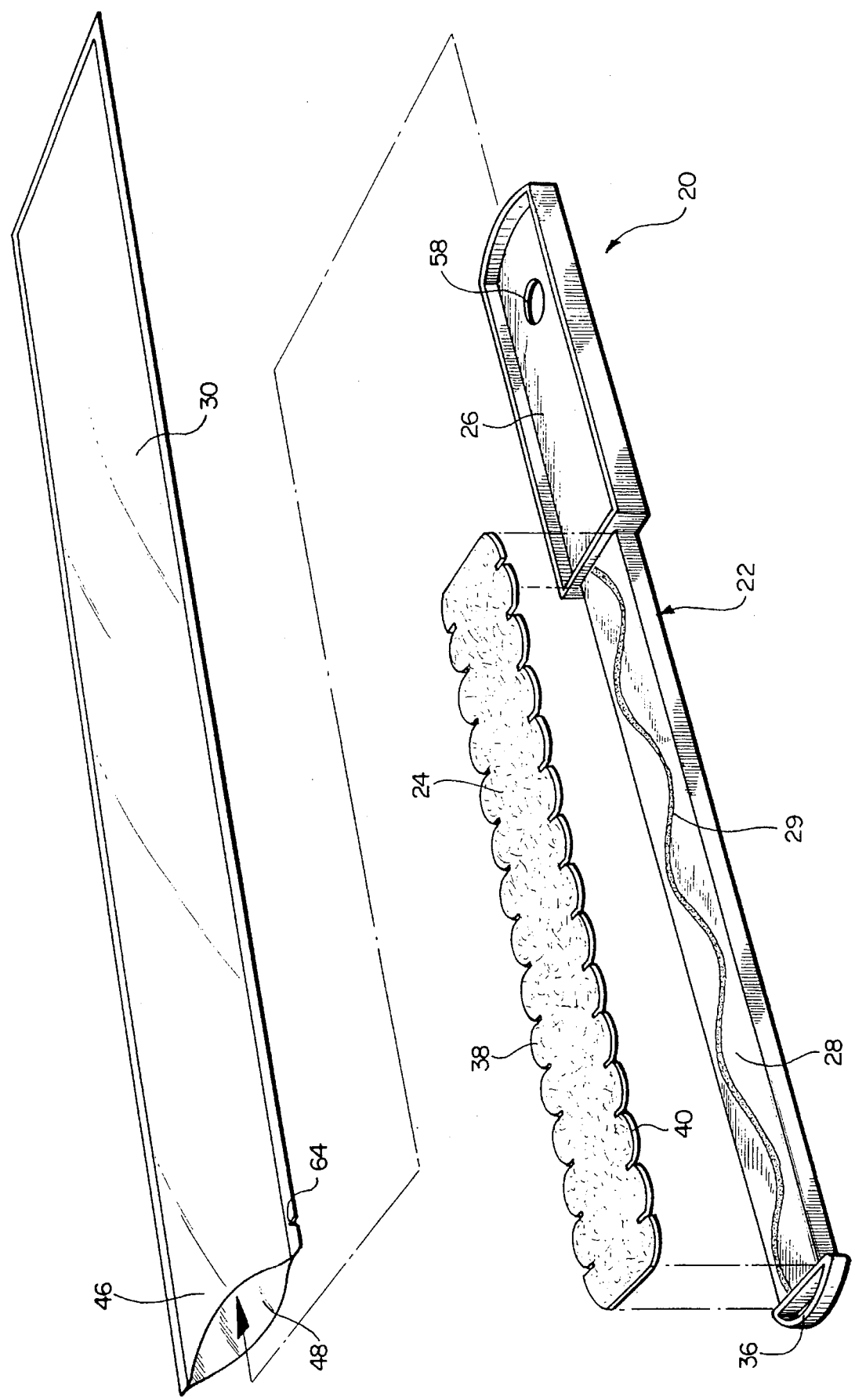
FIG. 1 is an exploded perspective view of a coagulation timer device which incorporates the features of a first embodiment of the invention of which include a carrier member, a medium and a bag member.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

A coagulation timer device 20, as illustrated in the drawings, includes a carrier member 22 and an absorbing medium 24. The coagulation timer device 20 is used to monitor the bleeding time of a patient before the patient undergoes surgery or other medical procedures. Generally, the medium 24 is touched at predetermined intervals to blood which results from an incision through the skin to measure the clotting time.

Figure 2:
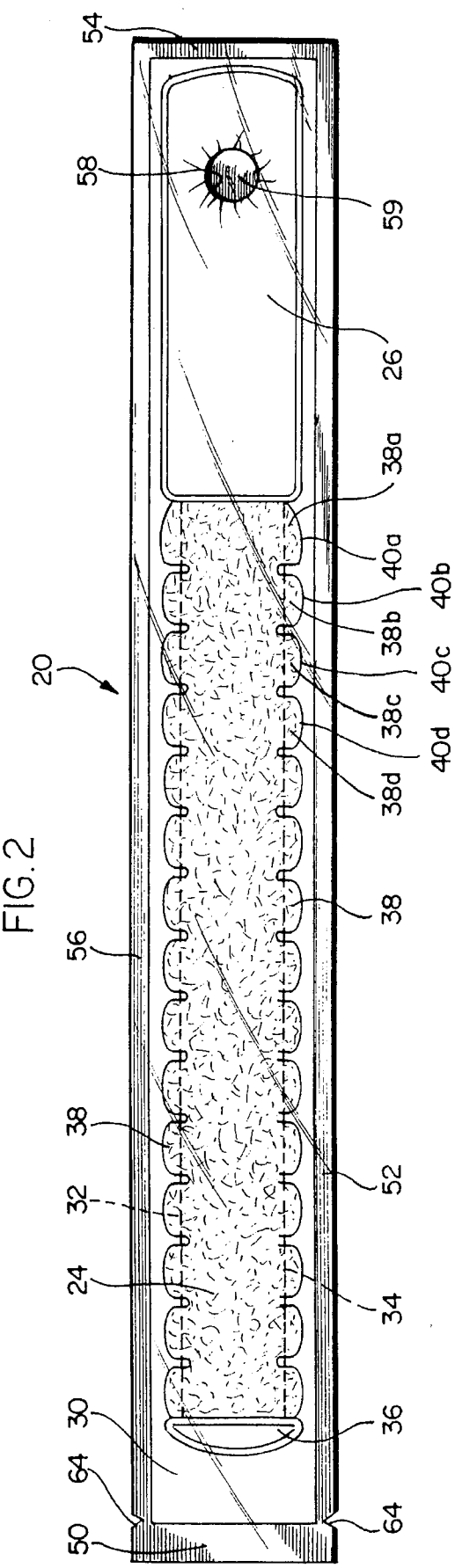
FIG. 2 is an elevational view of the coagulation timer device shown in FIG. 1 in a fully assembled configuration.

The carrier member 22 has a handle portion 26 and a linearly extending portion 28 which extends from the handle portion 26. The carrier member 22 is made of a suitable rigid material, preferably high density polystyrene, and can be made by known methods, such as molding. The rigidity of the carrier member 22 provides for increased control when the blood is being blotted. Initially, as shown in FIG. 2, the carrier member 22 and the absorbing medium 24 are enclosed and sealed within a sheath or bag member 30.

The linearly extending portion 28 is elongate with a proximal end, a distal end and side edges 32, 34. The linear portion 28 is integrally formed with the handle portion 26 which is at the proximal end of the linear portion 28. At the distal end of the linear portion 28, an end portion 36 may be included for reasons described herein.

The absorbing medium 24 is linearly oriented and is affixed to the linear portion 28 by known means, such as a layer of adhesive 29. The medium 24 extends generally the entire length between the end portion 36 and the handle portion 26. A suitable, known, absorbing material, preferably blotter paper or filter paper, may be used for the medium material.

The medium 24 includes a plurality of segments 38 whose use is described in detail herein. Each segment 38 is defined by a scalloped edge portion 40 which extends beyond the side edges 32, 34 of the linearly extending portion 28. Between each scalloped edge portion 38 is a cut-out portion which creates a gap 42 between each scalloped edge portion 38. The scalloped edge portion 38 serves several functions. First, the scallops clearly show a user where the medium 24 is to be touched to the blood. Second, the scalloped portion 38 controls the spread of blood. Third, since a gap 42 exists between each scalloped edge portion 38, the blood, when it is wicked, does not easily flow onto another segment 38.

Figure 3:
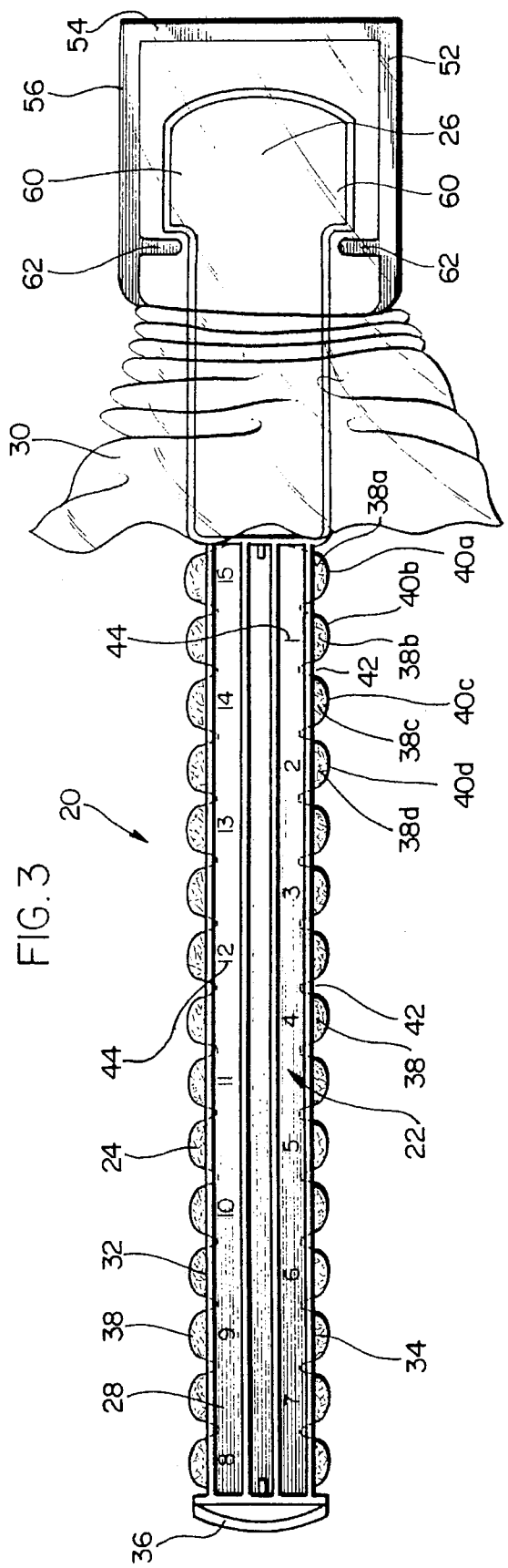
FIG. 3 is an elevational view of a coagulation timer device which incorporates the features of a second embodiment of the invention of which include a carrier member, a medium and a bag member, the bag member being in a retracted position.

The linear portion 28 includes a plurality of indicia 44, such as sequentially ordered numbers as illustrated in FIG. 3, on the opposite side of the linear portion 28 to which the medium 24 is attached. The indicia 44 runs adjacent to both edges 32, 34 of the linear portion 28 and each indicia 44 corresponds to a single segment 38 of the medium 24. The indicia 44 allows a medical person or technician to know where the medium 24 should be touched to the blood during the measurement of the patient's clotting time and provides a quick reference guide for the technician to know the total amount of time that it has taken for the blood to clot as described herein.

As shown in FIG. 3, a segment 38 is skipped between each indicia 44. Also, the indicia 44 on the adjacent to the opposite edges of the linear portion 28 do not lie directly across from each other. For example, as shown in FIG. 3, the segment 38c that is skipped between the numbers "1" and "2" lies directly across from the number "14" on the other side of the linear portion 28, but the segments 38b, 38d designated by "1" and "2" respectively, do not lie across from a numbered segment.

The sheath or bag member 30 encloses the carrier member 22 and the attached medium 24 therein and provides a protective container for packaging and maintaining the sterility of the coagulation timer device 20. The bag member 30 is made of two sheets 46, 48 of a suitable material, preferably polyethylene. The two sheets 46, 48 are hermetically sealed together by known methods, such as by heat sealing the edges 50, 52, 54, 56 of the sheets 46, 48 together. The bag member 30 is affixed to the handle 26 and is retractable around the handle portion 26 to uncover the medium 24 while being replaceable to cover the medium 24.

As shown in the drawings, the bag member 30 is transparent so that the coagulation timer device 20 can be seen. Of course, the bag member 30 may be colored without detracting from the scope of the invention. Furthermore, the bag member 30 may include a sticker or a label (not shown) on the outside of the bag member 30 on which the patient's name and other identifying data may be displayed.

Figure 4:
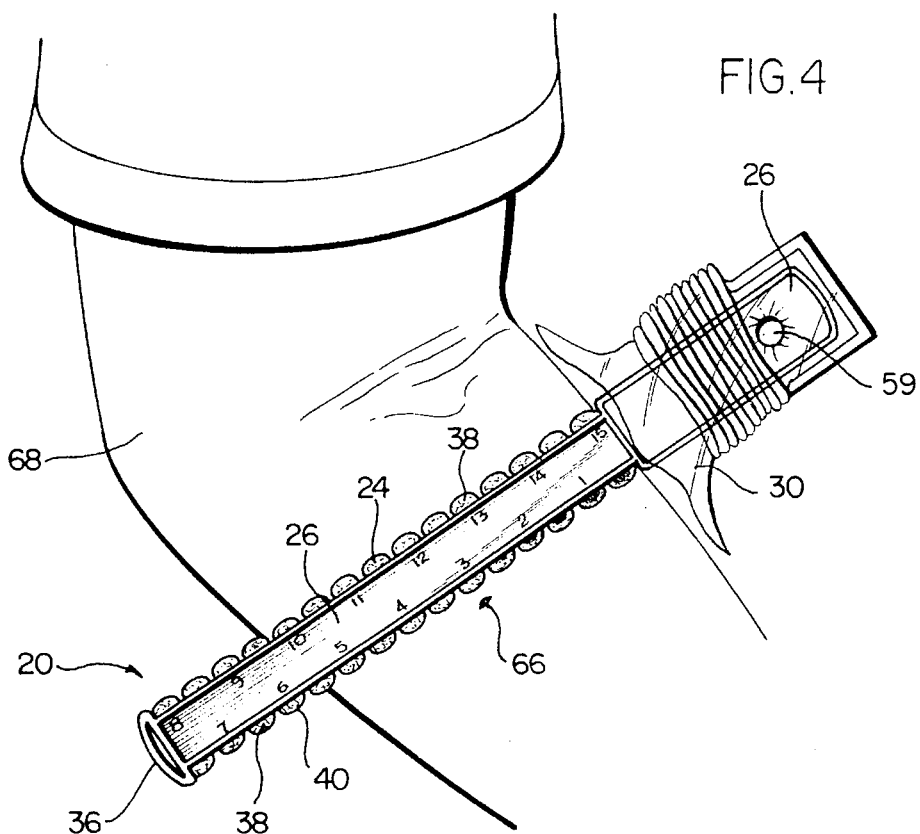
FIG. 4 is a perspective view of the coagulation timer device of FIG. 1, with the bag member in a retracted position, with the coagulation timer device being used on a patient.
Figure 5:
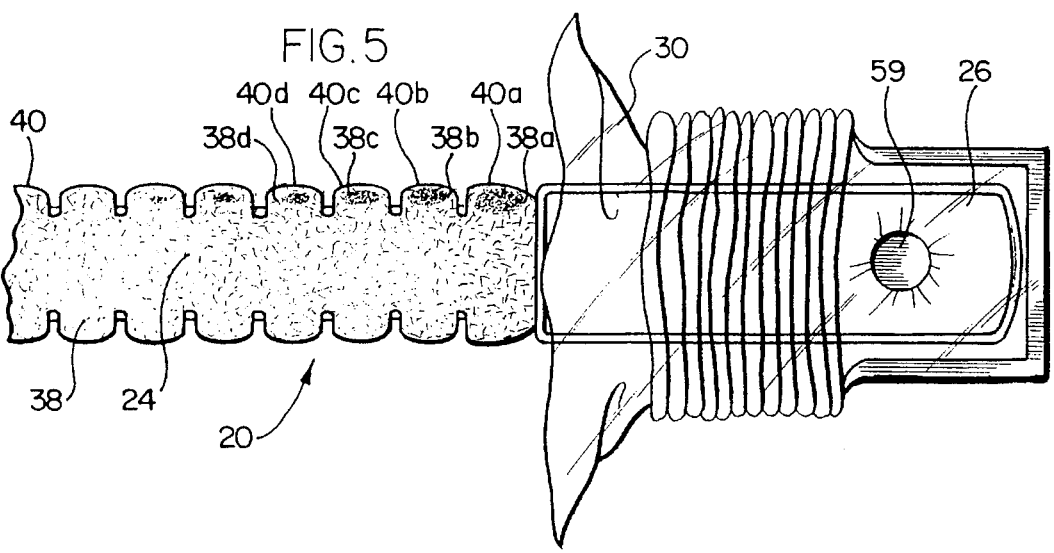
FIG. 5 is a partial elevational view of the coagulation timer device of FIG. 4 which more clearly illustrates how blood is collected on the device.

In a first embodiment, as shown in FIGS. 2 and 4–7, the handle portion 26 of the carrier member 22 includes a hole or aperture 58 therein. The bag member 30 is affixed through the hole 58 at 59 in the handle portion 26, by known methods, such as by heat sealing, heat staking, gluing or the like, the sheets 46, 48 of the bag member 30 together. Since the bag member 30 is attached to the handle portion 26, the bag member 30 will remain attached to the handle portion 26 when the bag member 30 is retracted around the handle portion 26 as shown in FIGS. 4 and 5.

In a second embodiment, as shown in FIG. 3, the handle portion 26 includes an enlarged portion or shoulder 60. The sheets 46, 48 of the bag member 30 are sealed together around the enlarged portion 60 at 62 by known methods, such as by heat sealing, heat staking, gluing or the like. When the bag member 30 is retracted around the handle portion 26 so as to uncover the medium 24, the bag member 30 remains attached to the handle portion 26, as shown in FIG. 3, since the bag member 30 is sealed at 62 around the shoulder 60. Alternatively, the handle portion 26 may include a notch (not shown) with the sheets 46, 48 of the bag member 30 being sealed together within the notch.

When a medical person or technician uses the coagulation timer device 20, the technician grasps the device 20 along the handle portion 26 which is covered by the bag member 30. Thus, the technician does not have to touch the medium 24 during the test and the risk of contact with the patient's blood is minimized.

The bag member or sheath 30 can include notches 64 at the end at which the bag member 30 is to be torn or cut open. The notches 64 lets a user know which end is to be opened (so the user will not tear open the bag member 30 at the end adjacent to the handle portion 26) and will aid in the bag member 30 being opened. Other indicia may be provided on the bag member 30 to let a user know which end is to be torn open.

As explained above, the linear portion 28 may include an end portion 36 at its distal end. While the coagulation timer device 20 as disclosed, only requires a user to use a single hand in administering the test, the user may additionally grasp the end portion 36 during testing or when medium 24 is being re-covered by the bag member 30 if necessary. If the technician grasps the end portion 26, the possibility of the technician grasping the medium 24 at a contaminated area is minimized.

Figure 6:
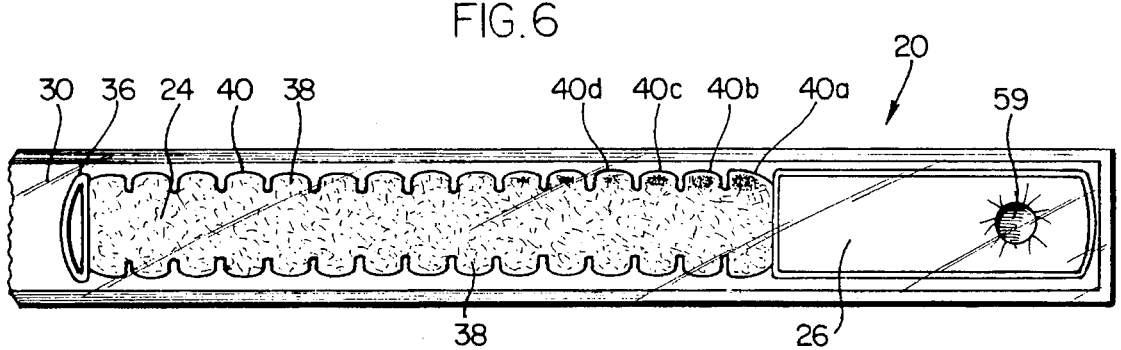
FIG. 6 is an elevational view of the coagulation timer device of FIGS. 4 and 5 with the bag member recovering the medium.

Now that the specifics of the novel coagulation timer device 20 of the present invention have been described, the method for using the coagulation timer device 20 will be explained in reference to FIGS. 4–6. First, an incision 66 of specified length and depth is administered through the skin of a patient 68. The incision 66 may be done by a known methods, such as a lancet as disclosed in U.S. Pat. No. 4,078,552 or U.S. Pat. No. 4,735,203. The incision 66 is made on the inside of the forearm of the patient 68, approximately five centimeters below the antecubital crease.

The distal end of the bag member 30 is ripped or cut off. The bag member 30 is slid back around the handle portion 26 to uncover the medium 24. The bag member 30 remains attached to the handle portion 26 as explained hereinabove with respect to the first embodiment shown in FIGS. 2 and 4–7 and the second embodiment shown in FIG. 3.

After the incision is made, a timer, such as a stop watch (not shown), is started. After a predetermined amount of time has passed, the medical person or technician touches the scalloped edge portion 40a of the medium 24 to the blood. The technician waits for a predetermined amount of time and then looks at the back side of the carrier member 22 to see where the number "1" is located and positions the coagulation timer device 20 over the incision 66. The technician then touches the scalloped edge portion 40b of the medium 24 to the blood at the position which corresponds to the number "1" and wicks the blood. This process continues with the technician wicking the blood at the next successive scalloped edge portion, for example 40c then 40d, until the blood does not stain the medium 24.

When the blood does not stain the medium 24, the timer is shut off and then the amount of time that has expired is recorded. The bleeding time is the amount of time from when the timer was started to when it was shut off. For example, if the predetermined amount of time the technician waits is thirty (30) seconds, as shown in FIG. 6, since six intervals have passed and on the seventh interval no staining occurred, as shown in FIG. 6, the clotting time is three minutes and thirty seconds. If thirty (30) seconds is used as the predetermined amount of time that passes between each wicking, then at "1", one minute will have passed; at "2", two minutes will have passed, and so on. Thus indicia provides the technician with a quick reference guide to know how much time passed before clotting was achieved.

The technician can wait until the completion of the test before re-covering the contaminated medium 24 with the bag member 30. Alternatively, the contaminated medium 24 can be re-covered with the bag member 30 between each wicking operation, if desired.

While preferred embodiments of the present invention are shown and described, it is envisioned that those skilled in the art may devise various modifications of the present invention without departing from the spirit and scope of the appended claims. The invention is not intended to be limited by the foregoing disclosure.

The invention claimed is:

1. A device for use in monitoring the bleeding time of a patient by administering an incision through the skin and then blotting the blood at predetermined intervals to determine the amount to time to achieve clotting, said device comprising:

a carrier member having a handle portion and a support portion extending therefrom;

an absorbing medium for use in blotting blood from the incision through the skin, said absorbing medium being affixed to said support portion;

a bag member overlying said absorbing medium, said bag member being affixed to the handle portion, retractable around said handle portion to uncover the absorbing medium, and replaceable to cover said absorbing medium.

2. A device as defined in claim 1, wherein said bag member is affixed to said handle portion by a heat stake.

3. A device as defined in claim 1, wherein said handle portion includes an enlarged portion, said bag member being affixed around said enlarged portion such that when said bag member is retracted to uncover the medium, the bag member remains attached to said handle portion.

4. A device as defined in claim 3, wherein said bag member is affixed around said enlarged portion by a seal.

5. A device for use in monitoring the bleeding time of a patient by administering an incision through the skin and then blotting the blood at predetermined intervals to determine the amount to time to achieve clotting, said device comprising:

a carrier member having a handle portion and a generally elongate extending support portion extending therefrom;

a generally planar, elongate absorbing medium for use in blotting blood from the incision through the skin, said absorbing medium being affixed to said generally elongate extending support portion and including a plurality of segments each defined by a scalloped edge portion which extends beyond an edge of the generally elongate extending support portion, said segments adapted to be used one at a time at predetermined intervals to blot the blood from the incision by touching the scalloped edge to the blood.

6. A device as defined in claim 5, wherein said generally elongate extending support portion includes indicia on an opposite side of said generally elongate extending support portion to which said absorbing medium is attached to allow a user to know where the absorbing medium should be touched to the blood at said predetermined intervals.

7. A device as defined in claim 5, wherein said absorbing medium is filter paper.

8. A device for use monitoring the bleeding time of a patient by administering an incision through the skin and then blotting the blood at predetermined intervals to determine the amount of time to achieve clotting, said device comprising: a generally planar absorbing medium for use in blotting blood from the incision, said generally planar absorbing medium including a generally planar scalloped edge portion providing a series of extending segments of said absorbing medium, said segments adapted to be used one at a time at predetermined intervals to blot the blood from the incision to determine the amount of time to achieve clotting.

9. A device as defined in claim 8, further including a carrier member to which said absorbing medium is mounted with said segments defined by the scalloped edge portion extending beyond an edge of said carrier member.

10. A device as defined in claim 9, further including a bag member affixed to said carrier member and being retractable to expose said segments defined by the scalloped edge portion and replaceable to cover said scalloped edge portion.

11. A device for monitoring the bleeding time of a patient by administering an incision through the skin and then blotting the blood at predetermined intervals to determine the amount of time to achieve clotting, said device comprising:

an absorbing medium for use in blotting blood from the incision, said absorbing medium including a scalloped edge portion providing a series of extending segments of said absorbing medium, said segments adapted to be used one at a time at predetermined intervals to blot the blood from the incision to determine the amount of time to achieve clotting; and indicia corresponding to said absorbing medium segments.

\* \* \* \* \*

UNITED STATES PATENT AND TRADEMARK OFFICE
CERTIFICATE OF CORRECTION

PATENT NO. : 5,572,997
DATED : November 12, 1996
INVENTOR(S) : Rowland W. Kanner and Fred E. Williams, Jr.

It is certified that error appears in the above-indentified patent and that said Letters Patent is hereby corrected as shown below:

On the title page item [56],
References Cited for U.S. Patent Documents :

-- 4,078,552    3/1978    Chen et al --

-- 4,735,203    4/1988    Ryder et al --

Signed and Sealed this

Twenty-ninth Day of April, 1997

Attest:

BRUCE LEHMAN

*Attesting Officer*    Commissioner of Patents and Trademarks